United States Patent [19]

Green et al.

[11] Patent Number: 5,293,881
[45] Date of Patent: Mar. 15, 1994

[54] REDUCED MASS ABSORBABLE SURGICAL FASTENER AND RETAINER

[75] Inventors: David T. Green, Westport; Henry Bolanos, East Norwalk; Robert J. Geiste, Milford, all of Conn.

[73] Assignee: United States Surgical Corporation, Norwalk, Conn.

[21] Appl. No.: 931,071

[22] Filed: Aug. 17, 1992

Related U.S. Application Data

[63] Continuation of Ser. No. 684,677, Apr. 11, 1991, abandoned.

[51] Int. Cl.$^5$ ............................................. A61B 17/00
[52] U.S. Cl. ............................... 128/898; 606/220
[58] Field of Search ............... 411/451; 606/151, 157, 606/158, 232, 220; 128/898, 220

[56] References Cited

U.S. PATENT DOCUMENTS

| | | | |
|---|---|---|---|
| D. 280,931 | 10/1985 | Green | D24/26 |
| D. 280,932 | 10/1985 | Green | D24/26 |
| D. 286,180 | 10/1986 | Korthoff | D24/26 |
| D. 286,441 | 10/1986 | Korthoff et al. | D24/26 |
| D. 286,442 | 10/1986 | Korthoff et al. | D24/26 |
| 4,060,089 | 11/1977 | Noiles | 606/232 |
| 4,402,445 | 9/1983 | Green | 227/19 |
| 4,506,670 | 3/1985 | Crossley | 606/232 |
| 4,513,746 | 4/1985 | Aranyl et al. | 227/19 |
| 4,534,350 | 8/1985 | Golden et al. | 128/334 |
| 4,534,352 | 8/1985 | Korthoff | 606/232 |
| 4,610,250 | 9/1986 | Green | 606/232 |
| 4,665,916 | 5/1987 | Green | 227/19 |
| 4,667,674 | 5/1987 | Korthoff et al. | 606/232 |
| 4,805,617 | 2/1989 | Bedi et al. | 606/232 |
| 4,932,960 | 6/1990 | Green et al. | 606/220 |

FOREIGN PATENT DOCUMENTS 0202090  11/1986  European Pat. Off.

OTHER PUBLICATIONS

EPO Search Report from Corresponding European Patent Application 92106241.0, dated Jul. 23, 1992.
Information Booklet for Auto Suture® Poly CS ™ 57 Disposable Loading Units (1988).

*Primary Examiner*—Stephen C. Pellegrino
*Assistant Examiner*—Gary Jackson

[57] ABSTRACT

A bioabsorbable surgical fastener comprising a fastener member and an interlocking retainer member. The surgical fastener has a total mass of less than 4 mg/transverse mm, thereby reducing the amount of foreign matter present at the wound site and facilitating faster resorption, while effecting hemostasis. The retainer member preferably has longitudinally extending slots on the lateral sides of the retainer for allowing transverse expansion of the columnar members into which the prongs of the fastener member are locked. Fins on both the lateral and transverse sides of the prongs provide extra strength, and stability during implantation. Stopping surfaces prevent the fastener's barbed tip from exiting the opposite side of the retainer.

10 Claims, 3 Drawing Sheets

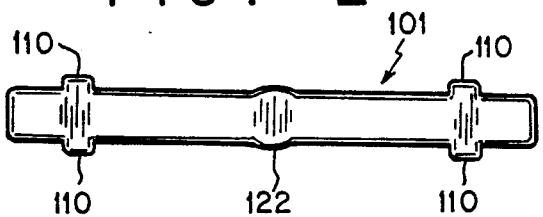
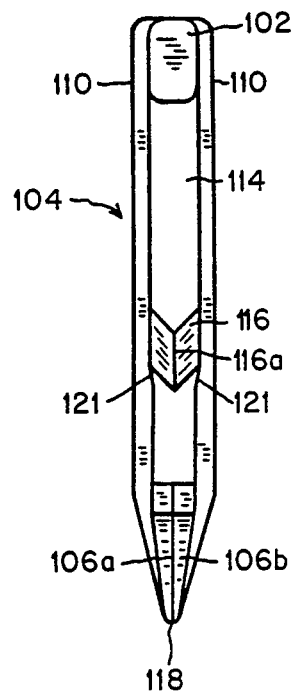
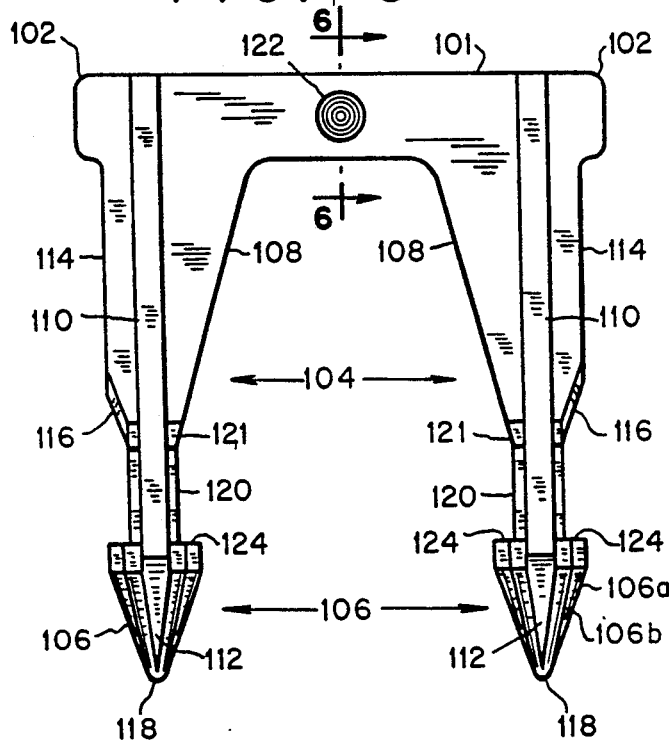
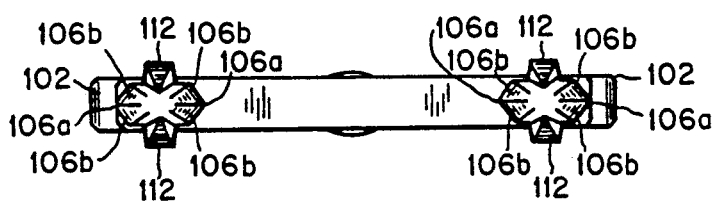
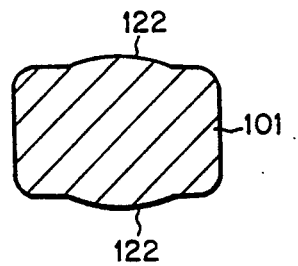

REDUCED MASS ABSORBABLE SURGICAL FASTENER AND RETAINER

This is a continuation of U.S. application Ser. No. 07/684,677 filed Apr. 11, 1991 now abandoned.

BACKGROUND OF THE INVENTION

1. Field of the Invention

This invention relates to surgical fasteners, and more particularly to two part bioabsorbable fasteners comprising a fastener member and retainer piece.

2. Background of Related Art

Surgical fasteners, or staples, are commonly used in surgical procedures to allow a surgeon to fasten body tissue quickly without the need for time-consuming suturing. Such surgical fasteners may be applied by surgical staplers singly, in succession, or a number may be applied simultaneously.

Some types of surgical fasteners are two-part devices. That is, they are composed of a fastener, or staple, portion, which is generally a pronged U-shaped member, and a retainer portion, which has apertures into which the prongs are engaged and held. Such fasteners, once engaged, are not separable. Therefore, once inserted into body tissue they cannot be easily removed. For this reason, two part fasteners are made of bioabsorbable material, such as glycolide, lactide, or copolymers of glycolide and lactide.

One such fastener is disclosed in U.S. Pat. No. 4,060,089 to Noiles. A fastener strip with multiple barbed prongs is disclosed, along with a retainer strip with a plurality of longitudinally spaced openings for receiving the prongs.

U.S. Pat. No. 4,402,445 to Green discloses a two pronged fastener with a retainer piece.

U.S. Pat. No. 4,506,670 to Crossley discloses a two part surgical fastener wherein the retainer piece is held to a supporting member by a lug with a frangible member. The prongs of the fastener, upon entering the aperture of the retainer, breaks the frangible member and pushes out the lug, thereby releasing the retainer piece from the supporting member.

U.S. Pat. No. 4,513,746 to Aranyi et al. discloses a two piece fastener. The fastener portion has two prongs with outer channels. The retainer piece has extensions with apertures for receiving the prongs of the fastener, and longitudinally extending expansion slots.

U.S. Pat. No. 4,805,617 to Bedi et al. discloses a surgical fastener system comprising parallel rows of staples and receivers with the receivers connected to adjacent receivers by a plurality of linkages.

U.S. Pat. No. 4,667,674 to Korthoff et al. discloses a surgical fastener having an extended base to reduce hemostasis.

U.S. Pat. No. 4,610,250 to Green discloses a two part surgical fastener. The fastener member has four prongs which mate with four openings in the retainer member. The two inner prongs are bent toward each other by camming surfaces in the corresponding openings in the retainer.

U.S. Pat. No. 4,932,960 to Green et al. discloses a two part surgical fastener in which the retainer member is provided with slot means to facilitate introduction of fastener prongs.

The following U.S. Design patents also illustrate fasteners: U.S. Pat. No. Des. 280,931; U.S. Pat. No. Des. 286,441; U.S. Pat. No. Des. 286,180; U.S. Pat. No. Des. 286,442 and U.S. Pat. No. Des. 280,932.

In designing and fabricating absorbable surgical fasteners and retainers, there are two competing considerations which must be addressed: first, the fastener/retainer combination must have sufficient mass to achieve effective hemostasis when applied to tissue and second, the fastener/retainer must not be so large as to remain in the body, i.e., fail to absorb, within a prescribed period of time.

Thus, for example, U.S. Pat. No. 4,534,352 to Korthoff discloses a surgical fastener member with an increased surface area to volume ratio to achieve faster resorption. Korthoff '352 teaches that this increased ratio does not sacrifice tensile strength retention during the period of time necessary for fastened tissue to heal and provides sufficient mass to penetrate tissue without buckling.

SUMMARY OF THE INVENTION

Accordingly, it is one object of the present invention to provide a two part bioabsorbable surgical fastener.

It is another object of the present invention to provide a two part surgical fastener which has sufficient mass to achieve effective hemostasis.

It is yet another object of the invention to provide a two part surgical fastener of reduced mass relative to prior fastener/retainer combinations so as to minimize the foreign matter introduced to the body and facilitate absorption thereof.

These and further objects and advantages are achieved herein by providing a two part surgical fastener comprising:
  a) a fastener member comprising
    i) a backspan defining a transverse axis;
    ii) at least two substantially parallel prongs extending substantially perpendicularly from the backspan; and
  b) a retainer member having
    i) a base
    ii) at least two columnar members, each columnar member having an aperture adapted to receive a respective one of the fastener prongs, said fastener member and retainer member having a total mass of less than 4 mg per transverse millimeter and, when engaged on tissue, being effective to achieve hemostasis.

BRIEF DESCRIPTION OF THE DRAWINGS

The accompanying figures, referred to herein and constituting a part hereof, illustrate preferred embodiments of the present invention, and together with the description, serve to explain the principles of the invention.

FIG. 2 shows a top view of the fastener portion of the invention;

FIG. 3 shows a side view of the fastener portion of the invention;

FIG. 4 shows a bottom view of the fastener portion of the invention;

FIG. 5 shows an edge view of the fastener portion of the invention;

FIG. 6 illustrates a cross sectional view of the retainer backspan;

DETAILED DESCRIPTION OF THE INVENTION

Two part bioabsorbable fasteners of the type described herein are typically applied by an apparatus such as that described in U.S. Pat. No. 4,655,916 to Green, the contents of which are herein incorporated by reference.

The surgical fastener of the present invention generally comprises a unitary plastic like retainer having at least two longitudinal columnar extensions with longitudinal apertures for receiving the distal ends of respective fastener prongs. The retainer is adapted to be positioned on the distal side of the body tissue to be fastened. The columns preferably each have at least one, and most preferably two, longitudinally extending expansion slots on the lateral sides of the column to facilitate transverse expansion of the column about the aperture.

The surgical fastener further comprises a unitary fastener portion initially separate from the retainer and having at least two distally extending prongs, the prongs being sufficiently rigid to pierce body tissue. The fastener portion is initially positioned on the proximal side of the body tissue to be fastened, and by means of a fastener applying apparatus, is moved distally through the body tissue such that the distal ends of the prongs, non-releasably engage the column. Preferably, the prongs, once engaged with the retainer columns, do not protrude beyond the bottom of the column.

Figure 1:
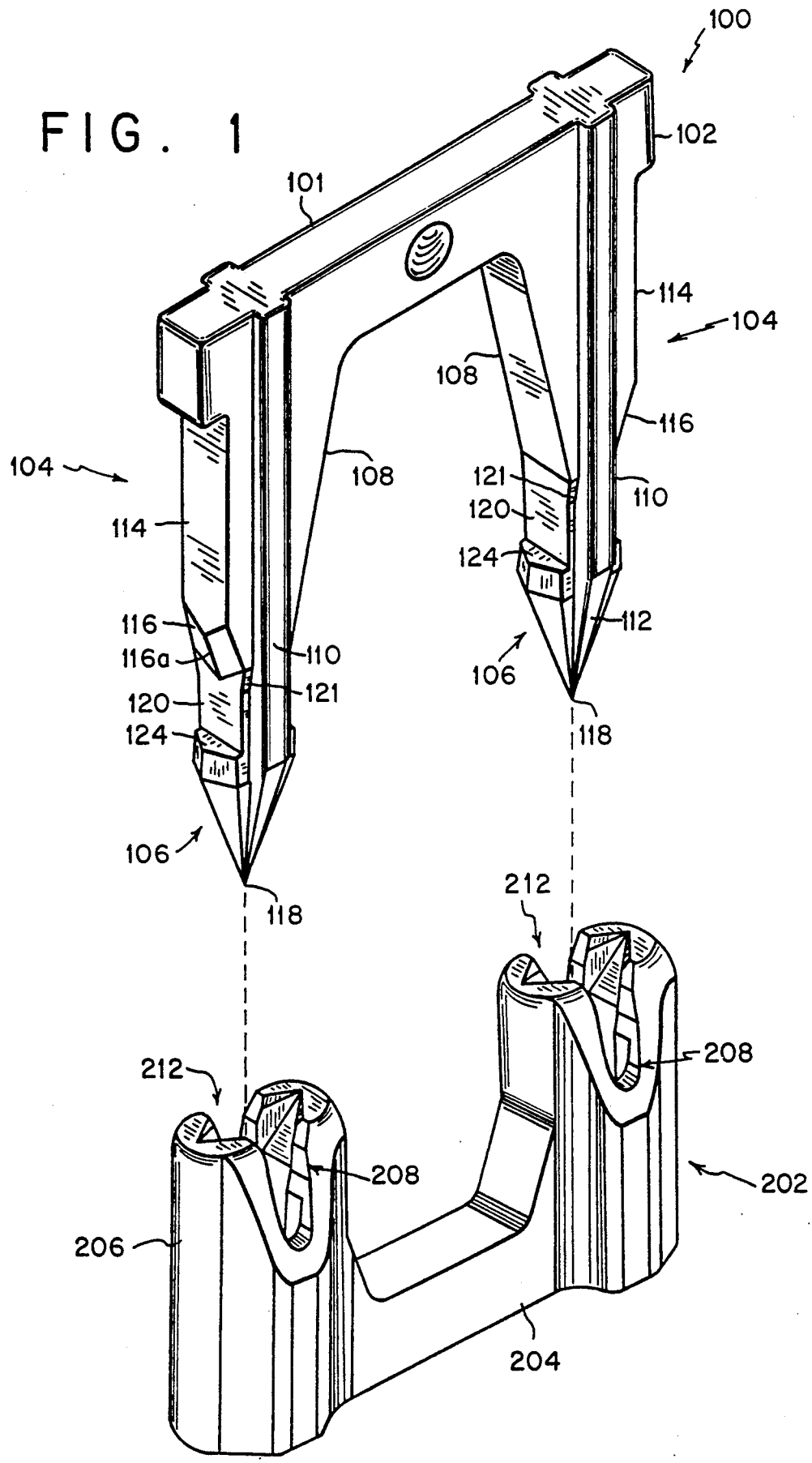
FIG. 1 shows a perspective view of a fastener and retainer of the present invention.
Figure 7:
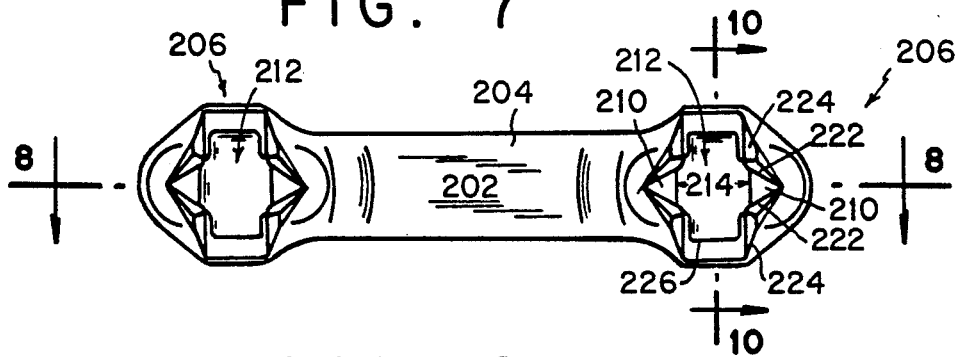
FIG. 7 shows a top view of the retainer.
Figure 8:
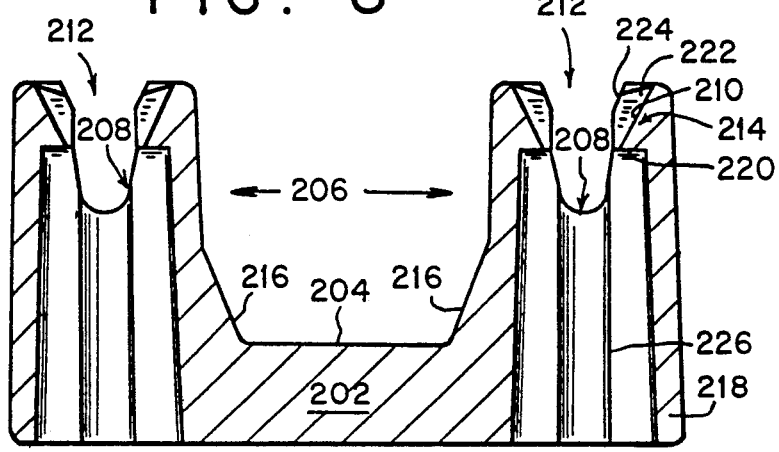
FIG. 8 shows a sectional side view of the retainer.
Figure 9:
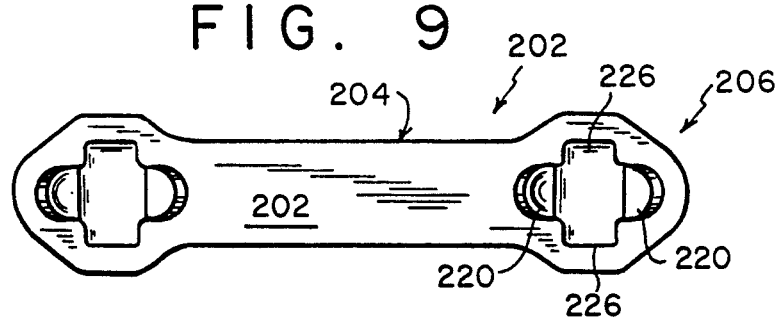
FIG. 9 shows a bottom view of the retainer.
Figure 10:
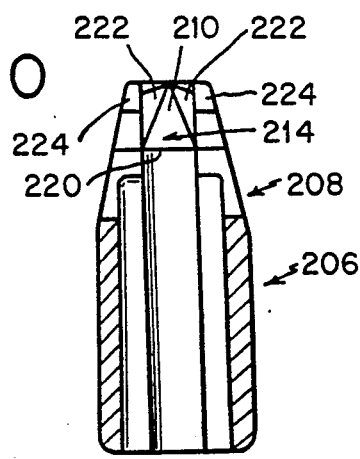
FIG. 10 shows a sectional view of a columnar member of the retainer.

FIG. 1 illustrates a preferred embodiment of the present invention. The U-shaped fastener portion 100 comprises a backspan 101 optionally with transversely projecting extensions 102 to improve hemostasis. As used herein, "hemostasis" refers to the arresting of bleeding of tissue, e.g., along an incision. Retainer 202 comprises columnar members 206 with apertures 212 and expansion slots 208, and base 204.

Prongs 104 extend substantially perpendicularly from the backspan 101 and are substantially parallel to each other. Prongs 104 each comprise a shank 120 and at least one barb 106 located at the distal end of the prong 104. Barbs 106 each terminate in a distal tip 118 for penetrating body tissue.

With respect to the discussion herein, the "longitudinal" direction, or the direction of the prongs, is the direction illustrated by the arrow Y. The "lateral" or "side by side" direction is the direction illustrated by arrow Z; the transverse direction, which is the direction of lengthwise extension of the backspan 101 and base 204, is illustrated by arrow X.

As illustrated in FIGS. 1, 2, 3, 4, 5 and 6, each prong preferably has two barbs 106 projecting from the inner and outer edge respectively of the shank 120 at the distal end of the prong. Alternatively the prongs may have one barb each. The barbs 106 each have a slicing edge 106a for cutting through body tissue, and preferably two wedging surfaces 106b for pushing aside tissue. Each barb 106 also comprises a proximal locking surface 124 which locks into the retainer piece 202 as explained below. Prongs 104 are supported by inside buttress members 108 which give added strength to prevent splaying of the prong as it enters the body tissue to be fastened. Buttress members 108 are substantially triangular shaped integral portions of the fastener which have an inner edge sloping from the backspan 101 to the shank 120.

Lateral fins 110 extend from the top of the backspan 101 to the barbs 106. Sloping surfaces 112 bring the fins 110 to the tips 118 of the barbs 106. Lateral fins 110 reinforce the prongs 104 to resist lateral deflection. Additionally, lateral fins 110 can act as guide rails in conjunction with a fastener applying apparatus to maintain the prongs in perpendicular alignment with the backspan and parallel alignment with each other as the fastener is being inserted into body tissue.

Each fin 114 extends along the outer transverse edge of each prong from the extension 102 of the backspan, to a terminal sloping surface 116 which inclines towards shank 120 in proximity to indentation 121 of said shank 120. The sloping surface 116 ideally possesses an edge 116a to facilitate the penetration of body tissue. In addition to facilitating the passage through body tissue, sloping surface 116 provides a means to lock the fastener 100 in the retainer 202 so that the barbs do not emerge from the opposite end of the apertures 212. This locking feature will be explained in more detail below.

Backspan 101 optionally has a protuberance 122 on each of the two lateral sides, as illustrated in FIGS. 2, 3 and 6. The protuberances perform no function with respect to the tissue fastening operation of the surgical fastener, but provide additional frictional contact with the interior surface of the loading and firing chamber of the fastener implanting instrument to prevent undesirable looseness.

Referring to FIGS. 1, 7, 8, 9 and 10, the retainer portion 202 possesses a base 204, and longitudinal columns 206 with apertures 212 for receiving the prongs 104 of fastener 100. The columns 206 also have longitudinally extending expansion slots 208 to permit transverse expansion of the entrance of aperture 212 in the lengthwise direction of the base 204 when the barb 106 enters the retainer 202.

Column 206 comprises projecting rims 214 having inclined longitudinally aligned camming surfaces 210, inclined guide slopes 222 for the wedging surfaces 106b of the barb 106, inclined guide slopes 224 for the lateral fins 110, and grooves 226 for lateral fins 110. The underside of rim portion 214 comprises a locking surface 220. The column walls 218 are gently inclined so that the aperture diameter widens from the rims to the exit. Columns 206 are braced by buttresses 216 to minimize splaying of the columns 206.

The fastener portion 100 and retainer portion 202 operate in conjunction to form a two piece interlocking surgical fastener. As the distal ends of the prongs 104 enter the respective apertures 212 of the retainer 202, the slicing edges 106a of the barbs 106 come into contact with the respective inclined camming surfaces 210 of the rim 214. Guide slopes 222 and 224 contact the wedging surfaces 106b and the lateral fins 110 respectively, thereby aligning the prongs. As the prongs are pushed into the retainer, the lateral expansion slots 208 allow the mouth of the aperture 212 defined by the opening between the rims 214 to expand transversely to accommodate the barbs 106. After the barbs 106 have passed the rims 214 the opening resiliently returns to its initial position thereby locking the fastener 100 within the retainer 202. Any forces tending to pull the fastener 100 out of the retainer 202 will cause the locking surface 124 of the barb 106 to abut the locking surface 220 of the rim 214. Thus, the fastener, once inserted in the retainer, cannot easily be removed. The terminal sloping surfaces 116 of fins 114 provide a stopping surface to limit the depth to which the prongs are inserted into the fastener. Such limiting of insertion depth confines the barbs 106 entirely within the interior of the column 206 and thereby prevents damage or irritation to body tissue which can be caused by the barb tips 118 protruding beyond the exit opening of the aperture 212.

The fastener portion 100 and retainer portion 202 are each integral constructions fabricated from bioabsorbable (or biodegradable) material such as polymers or copolymers of glycolide, lactide, p-dioxanone, polyester, trimethylene carbonate, polyamino acids, and the like. Surgical fasteners of the type described herein may be of any size appropriate to their function of fastening body tissue. However, the fastener and retainer members of the present invention are of reduced mass as compared to bioabsorbable fasteners used heretofore.

Unexpectedly, a reduction of mass in fastener and retainer members may be achieved without detrimentally affecting the efficacy of the fastener in achieving hemostasis. The engaged fastener of the invention has a mass of about 2 to about 4 milligrams per transverse millimeter, and preferably about 3 to about 3.5 mg/transverse mm. The mass reduction may be achieved by slimming the fastener and retainer members, in whole or in part, as compared to fasteners known heretofore. For example, the lateral dimensions of the backspan and prongs of the fastener, and the base and columnar members of the retainer member may be reduced by 20 to 35% relative to prior art fastener/retainer combinations without sacrificing hemostasis. Preferably, the transverse dimension of individual fastener/retainer combinations may be reduced, e.g., by about 20%, so that for a given incision to be fastened, a concomitant increase in the number of fastener/retainer combinations of the present invention, e.g. 20%, are used. A reduction in the transverse dimension of individual fastener and retainer elements helps to ensure effective molding and structural integrity of the pieces.

Although the dimensions of specific fastener/retainer combinations may differ based on the precise applications for which they are intended, a preferred set of dimensions are as follows:

| FASTENER A | | | |
|---|---|---|---|
| Structural element | Transverse | Longitudinal | Lateral |
| Fastener backspan 101 | 4.85 mm | 1.03 mm | 0.5 mm* |
| Prongs 104 | — | 5.64 mm | 0.5 mm* |
| Retainer base 204 | 5.15 mm | 0.76 mm | 0.76 mm |

*excluding fins 110; lateral dimension in region of fins 110 is 0.75 mm.

A second preferred set of dimensions are as follows:

| FASTENER B | | | |
|---|---|---|---|
| Structural element | Transverse | Longitudinal | Lateral |
| Fastener backspan 101 | 4.85 mm | 1.03 mm | 0.5 mm* |
| Prongs 104 | — | 4.88 mm | 0.5 mm* |
| Retainer base 204 | 5.15 mm | 0.76 mm | 0.76 mm |

*excluding fins 110; lateral dimension in region of fins 110 is 0.75 mm.

Although identical in a majority of dimensions, Fasteners A and B differ in the longitudinal dimension of prongs 104. Fastener A is particularly adapted to be used on tissue that compresses to approximately 4.3 mm whereas Fastener B is particularly suited for tissue that compresses to approximately 3.6 mm. One preferred application of the fasteners of the present invention is in performing a hysterotomy. In such application, Fastener A is generally applicable when the hysterotomy is scheduled or labor has been light, whereas Fastener B is generally applicable where labor has been prolonged, resulting in a thinning of the uterine wall.

EXAMPLE

Prior art fastener and retainer portions ("Control fasteners") were loaded into a cartridge of the type disclosed in U.S. Pat. No. 4,665,916 to Green. A total of sixteen (16) Control fasteners were so loaded, eight (8) Control fasteners on either side of a central knife channel creating two staple lines of approximately 57 mm. The transverse dimensions of the Control fastener portion and retainer portion were 6.2 mm and 6.6 mm, respectively. The length of the Control fastener portion prongs was approximately 5.6 mm. The Control fasteners were fabricated from a copolymer of glycolide and lactide (approximately 52 mole percent lactide, 48 mole percent glycolide) and each weighed approximately 33.8 mg. Thus, each Control fastener had a total mass of approximately 5.1 mg/mm.

A total of twenty (20) Fasteners A were also loaded into a cartridge of the type disclosed in U.S. Pat. No. 4,665,916 to Green, with ten (10) Fasteners A on either side of a knife channel forming two staple lines approximately 57 mm in length. Each Fastener A was fabricated from a glycolide/lactide copolymer (approximately 52 mole percent lactide, 48 mole percent glycolide) and weighed approximately 18.2 mg. Thus, each Fastener A had a total mass of approximately 3.52 mg/mm.

The Control fasteners and Fasteners A were each applied to tissue which compressed to approximately 4.3 mm. Fasteners A provided equivalent hemostasis to that achieved by the Control fasteners, despite the significantly lower mass/transverse mm of the Fasteners A. The lower mass/transverse mm of the Fasteners A advantageously reduced the amount of foreign material present at the would site and facilitated faster resorption of the glycolide/lactide copolymer. (Polyglycolic/polylactic acid copolymers degrade in-vivo by hydrolysis to glycolic acid and lactic acid which are then absorbed and metabolized by the body.)

It should be understood that while the above description contains many specifics, these specifics should not be construed as limitations on the scope of the invention, but merely as exemplifications of preferred embodiments thereof. Those skilled in the art will envision many other possible variations that are within the scope of and spirit of the invention as defined by the claims appended hereto.

We claim:

1. A method of repairing a wound achieving hemostasis while maintaining an amount of foreign material at the wound site to within a predetermined reduced range comprising:
   A) providing a fastener member comprising:
   a) a backspan defining a transverse axis; and
   b) at least two substantially parallel prongs extending substantially perpendicularly from said backspan;
   B) providing a retainer member having:
   a) a base; and
   at least two columnar members, each columnar member having an aperture adapted to receive a respective one of the fastener prongs; and said fastener member and retainer member having a total mass of less than about 4 mg per 5.7 transverse millimeters of fastened tissue edge;

C) engaging said fastener member and said receive member with tissue to achieve hemostasis.

2. The method of claim 1 wherein each of said columnar members is adapted to retain the distal end of a respective one of the prongs.

3. The method of claim 1 wherein each of said columnar members has slot means for allowing expansion of said apertures.

4. The method of claim 1 wherein said slot means allows expansion in the transverse direction.

5. The method of claim 1 wherein each of said prongs includes at least one lateral fin along a side thereof.

6. The method of claim 1 wherein said fastener is constructed from a bioabsorbable material.

7. The method of claim 6 wherein said bioabsorbable material is selected from the group consisting of polymers and copolymers of lactide, glycolide, p-dioxanone, polyester, trimethylene carbonate, and polyaminoacid.

8. The method of claim 1 wherein said fastener member and retainer member are sized and dimensioned for use on tissue which compresses to about 3.6 mm.

9. The method of claim 1 wherein said fastener member and retainer member are sized and dimensioned for use on tissue which compresses to about 4.3 mm.

10. The method of claim 1 additionally comprising means to lock the fastener prongs in the retainer member.

* * * * *